(12) United States Patent
McVey et al.

(10) Patent No.: US 12,017,009 B2
(45) Date of Patent: Jun. 25, 2024

(54) SYSTEM AND METHOD FOR ALTERING USER MIND-BODY STATES THROUGH EXTERNAL STIMULI

(71) Applicant: Therabody, Inc., Los Angeles, CA (US)

(72) Inventors: Amanda Jean McVey, Redondo Beach, CA (US); Timothy Roberts, Los Angeles, CA (US); Jason Wersland, Los Angeles, CA (US); Benjamin Nazarian, Los Angeles, CA (US); Jaime Sanchez Solana, Los Angeles, CA (US); Eduardo Merino, Los Angeles, CA (US); Michael Philips, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 17/933,423

(22) Filed: Sep. 19, 2022

(65) Prior Publication Data

US 2023/0398324 A1 Dec. 14, 2023

Related U.S. Application Data (60) Provisional application No. 63/352,005, filed on Jun. 14, 2022.

(51) Int. Cl.
*A61M 21/00* (2006.01)
*G16H 10/60* (2018.01)

(52) U.S. Cl.
CPC ............ *A61M 21/00* (2013.01); *G16H 10/60* (2018.01); *A61M 2021/0022* (2013.01);
(Continued)

(58) Field of Classification Search
CPC ................. A61M 21/00–02; A61B 5/165–168
See application file for complete search history.

(56) References Cited

U.S. PATENT DOCUMENTS

| 327,438 A | 9/1885 | Fuller |
|---|---|---|
| 1,545,027 A | 7/1925 | Ashlock |

(Continued)

FOREIGN PATENT DOCUMENTS

| CA | 107532 S | 9/2005 |
|---|---|---|
| CA | 126241 S | 6/2009 |

(Continued)

OTHER PUBLICATIONS

English translation of Cao (Year: 2000).*

(Continued)

*Primary Examiner* — Thaddeus B Cox
(74) *Attorney, Agent, or Firm* — Sterne, Kessler, Goldstein & Fox P.L.L.C.

(57) ABSTRACT

Disclosed herein are method, system, and computer-readable medium aspects for altering a user mind-body state through external stimuli. An aspect begins by onboarding a user through receipt of at least one data item. The aspect continues by receiving a mind-body state goal from the user and capturing the user's current mind-body state. The aspect then provides external stimuli to the user based on the at least one data item, the mind-body state goal, and the current mind-body state. The aspect captures a new mind-body state of the user after the external stimuli has been provided, and determines a similarity between the mind-body state goal and the new mind-body state. Based on the similarity, the aspect concludes by recommending further external stimuli to the user. In some aspects, the external stimuli corresponds to a category that is a predetermined combination of audio protocols, physical protocols, and behavioral cues.

17 Claims, 6 Drawing Sheets

(52) U.S. Cl.
CPC ............... *A61M 2021/0027* (2013.01); *A61M 2205/502* (2013.01); *A61M 2230/005* (2013.01)

(56) References Cited

U.S. PATENT DOCUMENTS

| | | | |
|---|---|---|---|
| 2,191,937 A | 2/1940 | Low |
| D143,678 S | 1/1946 | L. et al. |
| 2,987,334 A | 6/1961 | Wendling |
| 3,705,579 A | 12/1972 | Morini et al. |
| D230,522 S | 2/1974 | Norman |
| D242,666 S | 12/1976 | Smith |
| 4,046,142 A | 9/1977 | Whitney |
| 4,175,297 A | 11/1979 | Robbins et al. |
| D274,438 S | 6/1984 | Angerman et al. |
| D293,504 S | 1/1988 | Specht et al. |
| D308,980 S | 7/1990 | McGee |
| D314,001 S | 1/1991 | Nussbickl |
| D322,795 S | 12/1991 | Dianitsch |
| 5,103,809 A | 4/1992 | DeLuca et al. |
| D351,850 S | 10/1994 | Bolle |
| D352,726 S | 11/1994 | Bolle |
| D439,984 S | 4/2001 | Thach |
| 6,823,762 B2 | 11/2004 | Hu |
| D515,615 S | 2/2006 | Fecteau et al. |
| D519,147 S | 4/2006 | Moritz et al. |
| D550,750 S | 9/2007 | Chiang |
| D556,812 S | 12/2007 | Wang-Lee |
| D569,413 S | 5/2008 | Wong |
| 7,431,706 B2 | 10/2008 | Louis |
| D591,786 S | 5/2009 | Wang |
| D629,034 S | 12/2010 | McNeal et al. |
| D629,035 S | 12/2010 | Moritz et al. |
| 7,927,259 B1 | 4/2011 | Rix |
| 7,927,294 B2 | 4/2011 | Kamimura et al. |
| D649,577 S | 11/2011 | Goodman et al. |
| D653,695 S | 2/2012 | Tobia |
| D657,812 S | 4/2012 | Li |
| D659,644 S | 5/2012 | Gretz |
| D681,283 S | 4/2013 | Wang Lee |
| 8,473,045 B2 | 6/2013 | Terada et al. |
| D687,479 S | 8/2013 | Moritz et al. |
| D687,881 S | 8/2013 | Ginther et al. |
| D695,335 S | 12/2013 | Goodman et al. |
| D704,249 S | 5/2014 | Orzeck |
| 8,777,881 B2 | 7/2014 | Tsai |
| D711,961 S | 8/2014 | Arnette |
| D714,378 S | 9/2014 | Sandor |
| D716,364 S | 10/2014 | Chow et al. |
| D725,175 S | 3/2015 | Wang-Lee |
| D756,180 S | 5/2016 | Chen |
| D761,344 S | 7/2016 | Chen |
| D765,758 S | 9/2016 | Li |
| D765,759 S | 9/2016 | Li |
| D769,350 S | 10/2016 | Orzeck et al. |
| D781,288 S | 3/2017 | Park et al. |
| D784,441 S | 4/2017 | Garfias |
| D785,699 S | 5/2017 | Chen |
| D809,517 S | 2/2018 | Sakata et al. |
| 9,889,066 B2 | 2/2018 | Danby et al. |
| D817,732 S | 5/2018 | Rettler |
| D818,031 S | 5/2018 | Garfias |
| D820,258 S | 6/2018 | Maw et al. |
| D829,810 S | 10/2018 | Nellestam |
| D834,755 S | 11/2018 | Schempp |
| D837,395 S | 1/2019 | Gan |
| D868,878 S | 12/2019 | Langenwalter et al. |
| D895,830 S | 9/2020 | Nakamura |
| D899,502 S | 10/2020 | Liu |
| D900,435 S | 11/2020 | Huang et al. |
| D901,016 S | 11/2020 | Park et al. |
| D903,748 S | 12/2020 | Zhang |
| D906,406 S | 12/2020 | Lee et al. |
| D906,407 S | 12/2020 | Kim et al. |
| 10,881,849 B2 | 1/2021 | Pisarev et al. |
| D909,457 S | 2/2021 | Liang |
| D909,459 S | 2/2021 | Liang |
| D919,696 S | 5/2021 | Dong |
| D922,472 S | 6/2021 | Liang |
| D929,991 S | 9/2021 | Keller et al. |
| D944,885 S | 3/2022 | Choi et al. |
| 11,478,606 B1 | 10/2022 | English et al. |
| D975,090 S | 1/2023 | Deshmukh et al. |
| D978,232 S | 2/2023 | Deshmukh et al. |
| 2004/0044384 A1 | 3/2004 | Leber et al. |
| 2004/0237969 A1 | 12/2004 | Fuller |
| 2005/0146353 A1 | 7/2005 | Schwebel |
| 2006/0135890 A1 | 6/2006 | Tsai |
| 2006/0258930 A1 | 11/2006 | Wu et al. |
| 2009/0077749 A1 | 3/2009 | Roleder et al. |
| 2009/0216070 A1 | 8/2009 | Hunt et al. |
| 2013/0218197 A1 | 8/2013 | Tarumi |
| 2015/0190607 A1 | 7/2015 | Sugio et al. |
| 2016/0367425 A1 | 12/2016 | Wersland |
| 2016/0374886 A1 | 12/2016 | Wyatt et al. |
| 2017/0042754 A1 | 2/2017 | Fowers et al. |
| 2017/0131553 A1 | 5/2017 | Pletenetskyy et al. |
| 2017/0246076 A1 | 8/2017 | Miller et al. |
| 2017/0252534 A1 | 9/2017 | Nofzinger |
| 2017/0304145 A1 | 10/2017 | Pepe |
| 2017/0340270 A1* | 11/2017 | Ganesh ............... A61B 5/4836 |
| 2018/0099143 A1 | 4/2018 | Kim et al. |
| 2018/0141188 A1 | 5/2018 | Lai |
| 2019/0029878 A1 | 1/2019 | Linder et al. |
| 2019/0053948 A1 | 2/2019 | Schempp |
| 2020/0170534 A1* | 6/2020 | Flaeschner ........... A61B 5/7264 |
| 2020/0219615 A1* | 7/2020 | Rabin ................. G05B 19/416 |
| 2020/0306493 A1 | 10/2020 | Lee |
| 2020/0352821 A1 | 11/2020 | Wersland et al. |
| 2021/0022955 A1 | 1/2021 | Wersland et al. |
| 2021/0128399 A1 | 5/2021 | Wersland et al. |
| 2021/0220210 A1 | 7/2021 | Berdahl et al. |
| 2021/0244611 A1 | 8/2021 | Wersland et al. |
| 2021/0259557 A1* | 8/2021 | Frank ...................... G01J 3/50 |
| 2021/0286180 A1 | 9/2021 | Samec et al. |
| 2021/0330539 A1 | 10/2021 | Faussett |
| 2021/0401663 A1 | 12/2021 | Wersland et al. |
| 2022/0105359 A1 | 4/2022 | Rappaport |
| 2022/0241137 A1 | 8/2022 | Solana et al. |
| 2022/0257962 A1* | 8/2022 | Mogen ................. A61B 5/4836 |
| 2023/0001131 A1 | 1/2023 | English et al. |
| 2023/0001191 A1 | 1/2023 | Schwarz et al. |

FOREIGN PATENT DOCUMENTS

| | | |
|---|---|---|
| CN | 2400107 Y * | 10/2000 |
| CN | 201239336 Y | 5/2009 |
| CN | 301664182 S | 9/2011 |
| CN | 202637439 U | 1/2013 |
| CN | 103550029 A | 2/2014 |
| CN | 303250924 S | 6/2015 |
| CN | 303250929 S | 6/2015 |
| CN | 303793818 | 1/2016 |
| CN | 303798351 | 8/2016 |
| CN | 303826703 | 8/2016 |
| CN | 304016902 | 1/2017 |
| CN | 106511045 A | 3/2017 |
| CN | 106859949 A | 6/2017 |
| CN | 304337489 | 10/2017 |
| CN | 304402475 | 12/2017 |
| CN | 304461942 | 1/2018 |
| CN | 304561844 S | 3/2018 |
| CN | 304795155 | 8/2018 |
| CN | 207855923 U | 9/2018 |
| CN | 304875170 | 11/2018 |
| CN | 108938359 A | 12/2018 |
| CN | 304934022 | 12/2018 |
| CN | 304982787 | 1/2019 |
| CN | 109528473 A | 3/2019 |
| CN | 305250747 | 7/2019 |
| CN | 305275902 | 7/2019 |
| CN | 305302847 | 8/2019 |
| CN | 305318901 | 8/2019 |
| CN | 305327420 | 8/2019 |

(56) References Cited

FOREIGN PATENT DOCUMENTS

| | | |
|---|---|---|
| CN | 305349253 | 9/2019 |
| CN | 305501003 | 12/2019 |
| CN | 305555921 | 1/2020 |
| CN | 305611712 | 2/2020 |
| CN | 210228475 U | 4/2020 |
| CN | 305726159 | 4/2020 |
| CN | 305738333 | 4/2020 |
| CN | 305775702 | 5/2020 |
| CN | 305852653 | 6/2020 |
| CN | 305872601 | 6/2020 |
| CN | 211067931 U | 7/2020 |
| CN | 305982060 | 8/2020 |
| CN | 305989858 | 8/2020 |
| CN | 306004590 | 8/2020 |
| CN | 306383446 | 9/2020 |
| CN | 306119091 | 10/2020 |
| CN | 306130382 | 10/2020 |
| CN | 306142072 | 10/2020 |
| CN | 306184674 | 11/2020 |
| CN | 306197232 | 11/2020 |
| CN | 306242891 | 12/2020 |
| CN | 306339053 | 2/2021 |
| CN | 306339102 | 2/2021 |
| CN | 306423578 | 3/2021 |
| CN | 306532932 | 5/2021 |
| CN | 306554191 | 5/2021 |
| CN | 213311563 U | 6/2021 |
| CN | 306623311 | 6/2021 |
| CN | 306682839 | 7/2021 |
| CN | 306724806 | 7/2021 |
| CN | 306754485 | 8/2021 |
| CN | 306778555 | 8/2021 |
| CN | 306798663 | 8/2021 |
| CN | 113679585 A | 11/2021 |
| CN | 306922350 | 11/2021 |
| CN | 214971144 U | 12/2021 |
| CN | 307035688 | 12/2021 |
| CN | 113952201 A | 1/2022 |
| CN | 215425988 U | 1/2022 |
| CN | 215606829 U | 1/2022 |
| CN | 307073094 | 1/2022 |
| CN | 215739868 U | 2/2022 |
| CN | 215839897 U | 2/2022 |
| CN | 307138150 | 3/2022 |
| CN | 307160397 | 3/2022 |
| CN | 216258666 U | 4/2022 |
| EM | 000131743-0001 | 5/2004 |
| EM | 000745187-0001 | 7/2007 |
| EM | 001620709-0003 | 10/2009 |
| EM | 001250096-0001 | 12/2010 |
| EM | 002278416-0003 | 7/2013 |
| EM | 003734482-0001 | 2/2017 |
| EM | 006062022-0002 | 1/2019 |
| EM | 007837737-0005 | 4/2020 |
| EM | 007837737-0007 | 4/2020 |
| EM | 007837737-0014 | 4/2020 |
| EM | 008150635-0004 | 9/2020 |
| GB | 3024419 | 5/2006 |
| GB | 90005087670001 | 6/2006 |
| GB | 90007451870001 | 7/2007 |
| GB | 80767100001000 | 8/2011 |
| GB | 90037344820001 | 2/2017 |
| GB | 90058325810001 | 12/2018 |
| GB | 90060620220002 | 1/2019 |
| GB | 90078377370005 | 4/2020 |
| GB | 90078377370007 | 4/2020 |
| GB | 90078377370014 | 4/2020 |
| JP | S5428491 A | 3/1979 |
| JP | H0447440 U | 4/1992 |
| JP | 2000189525 A | 7/2000 |
| JP | 2011502369 A | 1/2011 |
| JP | 5129032 B2 | 1/2013 |
| JP | 2014511240 A | 5/2014 |
| KR | 300619292 | 11/2011 |
| KR | 101162978 B1 | 7/2012 |
| KR | 20170108550 A | 9/2017 |
| KR | 300925482 | 10/2017 |
| RU | 00118501 | 1/2020 |
| SG | 181413 A1 | 7/2012 |
| TW | I359657 B | 3/2012 |
| WO | WO-D07671-0001 | 9/2011 |
| WO | WO-2012074483 A1 | 6/2012 |
| WO | WO-2018013835 A4 | 3/2018 |
| WO | WO-2020149532 A2 | 7/2020 |
| WO | WO-D207075-001 | 9/2020 |
| WO | WO-D207075-002 | 9/2020 |
| WO | WO-2020219350 A1 | 10/2020 |
| WO | WO-2022056340 A1 | 3/2022 |
| WO | WO-2023172676 A2 | 9/2023 |

OTHER PUBLICATIONS

Amazon: "BOMOCO Eye Massager with Heat and Vibration, AI Intellignet Voice Control Relxation Gifts for Women Men Rechargeable Intelligent Eye Mask," Posted at amazon.com, Posting date Apr. 27, 2022, [online], 9 Pages, [Site visited on Dec. 11, 2022], Retrieved from URL: https://www.amazon.com/dp/B09YY9B3W4/.

Amazon: "Breo iSee4 Eye Massager with Heat, Electric Massager for Dry Eye, Eye Strain, Eye Fatigue Relief & Better Sleep," Posted at Amazon.com, Posting date Jul. 7, 2020, [online], 10 Pages, [Site visited Dec. 11, 2022] Retrieved from URL: https://www.amazon.com/dp/B08CGS7C16/.

Amazon: "Cfeneyol Eye Massager, Smart Eye Mask With Heating Pads, Warm Compress For Dry Eyes, Weighted Sleep Mask With Vibration For Eye Tension Relief, Christmas Gifts For Men," posted at amazon.com, Posting date Nov. 3, 2021, [online], 9 Pages, [Site visited on Dec. 11, 2022], Retrieved from URL: https://www.amazon.com/dp/B09KX3J2KP.

Amazon: "Eye Massager with Airbag Kneading, Constant Temperature Hot Compress, Multi-Frequency Vibration and Bluetooth Music (L, White)," TLINNA, First available Nov. 12, 2019, 10 Pages, Retrieved from URL: https://www.amazon.com/Massager-Temperature-Multi-Frequency-Vibration-Bluetooth/dp/B09PR7C6NC/ref=dp_coos_1?pd_rd_i=B09PR7C6NC&psc=1.

Amazon: "RENPHO Eye Massager with Heat, Compression, Remote Control, Bluetooth, Eye & Temple Massage Mask for Relax Eye Strain, Reduce Dark Circles, Dry Eyes, Improve Sleep, Christmas Gifts Delay Eye Aging," Posted at amazon.com, Posting date Jul. 16, 2020, [online], 15 Pages, [Site visited Dec. 11, 2022], Retrieved from URL: https://www.amazon.com/RENPHO-Updated-Compression-Bluetooth-Rechargeable/dp/B088BJ8B1G.

Anthony Katz, "The RAPTOR: Helps Patients and Saves Your Most Valuable Tool . . . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.

Deanlong: "How Does An Eye Massager Help in Eye Strain & Eye Fatigue Relief?," Jun. 14, 2022, 17 Pages, Downloaded Nov. 22, 2022, Retrieved from URL: https://www.deanlong.io/blog/how-does-an-eye-massager-help-in-eye-strain-eye-fatigue-relief.

Defendant's Initial Invalidity Contentions, *Therabody, Inc. v. Tzumi Electronics LLC et al.*, Case No. SDNY-1-21-cv-07803 (PGG)(RWL), dated Aug. 17, 2022; 16 pages.

Description of Therabody GI Device, available at: https://www.therabody.com/us/en-us/faq/thearagun-devices/faq-devices-1.html?fdid=faq&csortb1=sortOrder&csortd1=1 (last visited Feb. 15, 2023).

Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.

International Search Report and Written Opinion for International Application No. PCT/US2023/019392 dated Aug. 3, 2023, 15 pages.

Madaus S., "The Therabody SmartGoggles, High-Tech Device Brings the Theragun Treatment to your Eyes," Posted at self.com, Posting date Sep. 20, 2022, [online], 12 Pages, [site visited Nov. 12, 2022], Retrieved from URL: https://www.self.com/story/therabody-smartgoggles.

(56) References Cited

OTHER PUBLICATIONS

Mazzagers: "An Eye Massage Greatly Reduces Stress, Anxiety and Promotes Good Mental Health," Jan. 17, 2020, 06 Pages, Nov. 22, 2022, Retrieved from URL: https://mazzagers.com/eye-massager-stress-relief/.

RHMIP: "Eye Massager With Heat, Bluetooth Music Rechargeable Eye Heat Massager, Relax and Reduce Eye Starin Dark Circles Eye Bags Dry Eye, Ldeal Gift for Both Men and Women (White)," Posted at Amazon.com, Posting date Oct. 23, 2021, [online], 10 Pages, [Site visited Dec. 11, 2022], Retrieved from URL: https://www.amazon.com/dp/B09K4LK8ZQ/.

SereneLife: "SereneLife SLEYMSG40 Smart Eye Massager with Heat and Presssure Point Therapy," posted atwalmart.com, posting date Nov. 30, 2021, [online], 9 Pages, [site visited Dec. 11, 2022], Retrieved from URL: https://www.walmart.com/ip/SereneLife-SLEYMSG40-Smart-Eye-Massager-with-Heat-Pressure-Point-Therapy/390691257.

Venkatesan S., Dr., MD., "Oculo Cardiac Reflex: An Unique Neural Link Between the Eyes and Heart," Feb. 3, 2015, 7 Pages, Nov. 22, 2022, Retrieved from URL: https://drsvenkatesan.com/tag/eye-ball-massage/.

Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.

Visual Description of Hyper Ice, Inc. Raptor Device, "RAPTOR Solutions 1.3 Prone," available at: https://www.youtube.com/watch?v=6i1tRqdwPU8&t=156s (last visited Feb. 15, 2023); 1 page.

\* cited by examiner

SYSTEM AND METHOD FOR ALTERING USER MIND-BODY STATES THROUGH EXTERNAL STIMULI

BACKGROUND

Technical Field

Aspects of the present disclosure relate to components, systems, and methods for altering user mind-body states through external stimuli.

Background

The mind and the body are connected. A person's physical health affects their mind, just as the state of their mind influences their body. Taking steps to improve their physical health can help a person's mind, and vice versa.

Engaging in intentional mind-body practices to help change or regulate a person's mind-body state can be important for optimal performance and well-being. A number of mind-body practices, such as yoga and meditation, are well known. Engagement in these sorts of mind-body practices can provide various health benefits, such as reducing blood pressure, heart rate, respiratory rate, stress, anxiety, and pain intensity. Mind-body practices can also be used to improve immune response, neural connectivity, and arousal levels.

Successful engagement in mind-body practices such as yoga and meditation often requires training by and practice with an instructor or coach, and learning and following formal techniques. There can be a steep learning curve associated with these practices and mastering their techniques. And these mind-body practices are often conducted in the absence of external stimuli, or with only limited external stimuli such as music, so that the person engaged in the activity can focus on their practice and techniques. Moreover, even when some form of external stimuli is used, the external stimuli is often generically designed and is often generically presented with a one-size-fits-all approach that does not factor in the user's present mind-body state or their mind-body goals.

SUMMARY

Accordingly, there is a need for new and improved systems and methods for altering user mind-body states through external stimuli, some of which can address one or more of the above issues.

In aspects presented herein, user input devices, audio devices, physical stimuli devices, biometric sensors, and computing devices can work together to alter a user's mind-body state.

In an aspect, an example system for altering a user mind-body state through external stimuli is described. The example system can include one or more user input devices, biometric sensors, audio devices, physical stimuli devices, and computing devices. The computing devices can be coupled to one or more of the user input devices, the biometric sensors, the audio devices, and the physical stimuli devices. The computing devices can also include a processor and a memory, wherein the memory can contain instructions stored thereon that when executed by the processor cause the computing devices to perform certain operations.

In one aspect, the computing devices can first on-board a user through receipt of at least one data item from the user input devices. The computing devices can then receive a mind-body state goal from the user through the user input devices and can capture a current mind-body state of the user through the user input devices and/or the biometric sensors. The computing devices can continue by providing external stimuli to the user based on the at least one data item, the mind-body state goal, and the current mind-body state, via the one or more audio devices and/or the physical stimuli devices. After providing the external stimuli, the computing devices can capture a new mind-body state of the user through the user input devices and/or the biometric sensors, and determines a similarity between the mind-body state goal and the new mind-body state. The computing devices can then recommend further external stimuli to the user through the user input devices based on the similarity.

In another aspect, an example method for altering a user mind-body state through external stimuli is described. The method can begin by onboarding a user through receipt of at least one data item. The method can continue by receiving a mind-body state goal from the user and capturing the user's current mind-body state. The method then provides external stimuli to the user based on the at least one data item, the mind-body state goal, and the current mind-body state. The method captures a new mind-body state of the user after the external stimuli has been provided, and determines a similarity between the mind-body state goal and the new mind-body state. Based on the similarity, the method concludes by recommending further external stimuli to the user.

Further features and advantages, as well as the structure and operation of various aspects, are described in detail below with reference to the accompanying drawings. It is noted that the specific aspects described herein are not intended to be limiting. Such aspects are presented herein for illustrative purposes only. Additional aspects will be apparent to persons skilled in the relevant art based on the teachings contained herein.

BRIEF DESCRIPTION OF THE DRAWINGS

The accompanying drawings, which are incorporated herein and form a part of the specification, illustrate aspects of the present disclosure and, together with the description, further serve to explain the principles of the disclosure and to enable a person skilled in the pertinent art to make and use the disclosure.

In the drawings, like reference numbers generally indicate identical or similar elements. Additionally, generally, the left-most digit of a reference number identifies the drawing in which the reference number first appears.

Aspects of the present disclosure will be described with reference to the accompanying drawings.

DETAILED DESCRIPTION

Provided herein are method, system, and/or computer-readable medium aspects, and/or combinations and sub-combinations thereof for altering a user mind-body state through external stimuli to enhance performance and well-being.

Aspects herein describe an innovative platform that can provide a user with external stimuli, such as audio and/or physical stimuli, to alter their mind-body state to enhance performance and well-being. The innovative platform can provide an auditory experience capable of altering the mind-body state of a user. The innovative platform can be capable of combining this auditory experience with a physical experience. For example, as a predetermined audio experience is playing for the user, a linked physical experience can be physically stimulating a portion of the user's body. Such a multi-sensory experience can be provided based on a user's mind-body state goal, which can fall into one or more predetermined mind-body goal categories corresponding to desired mind-body states. In addition, the innovative platform can be implemented with an intelligent recommendation engine that considers user input, biofeedback from biosensors, and prior use effectiveness to curate the multi-sensory experience for the user. For example, based on a user's self-reported energy level, their desired mind-body state, their heart rate, and/or data from a prior use with a particular experience, the innovative platform can suggest a specific multi-sensory experience to be conducted for a certain duration.

Aspects herein can provide various benefits. For example, by providing a multi-sensory experience, the innovative platform can take advantage of the principle of entrainment. Entrainment is the simultaneous activation of neurons from different parts of the brain. For example, when a person hears a rhythmic sound, it activates their auditory system and also engages their motor system. In this example, a physical stimuli can be applied at a similar rhythm, further syncing the two systems. In other words, a multi-sensory experience can cause a person to achieve certain health benefits faster. In another example, by providing personalized external stimuli through an intelligent recommendation engine, the innovative platform can respond to the user's needs and preferences. Based on the various inputs and parameters from the user, the intelligent recommendation engine can constantly improve the type and quality of external stimuli provided to the user. Therefore, the innovative platform that can deliver a multi-sensory experience via targeted external stimuli can improve upon the shortcomings of current systems and methods by improving the user's experience during use.

Figure 1:
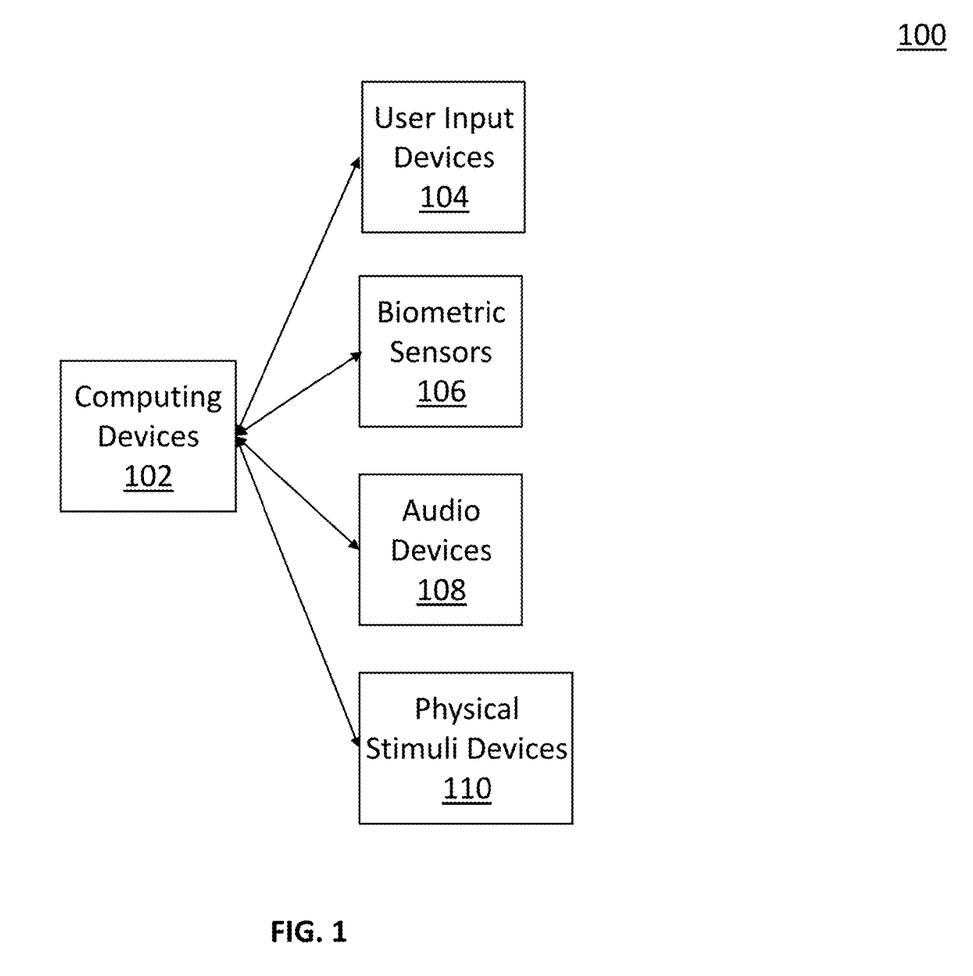
FIG. 1 is a block diagram of a system for altering a user mind-body state through external stimuli, according to some aspects of the present disclosure.

FIG. 1 is a block diagram of a system 100 for altering a user mind-body state through external stimuli, according to some aspects of the present disclosure. System 100 can include one or more computing devices 102, user input devices 104, biometric sensors 106, audio devices 108, and physical stimuli devices 110.

Computing devices 102 can be any well-known computers, having a processor and a memory, capable of performing the functions described herein. Computing devices 102 can be the same or similar to computer system 400 described below with reference to FIG. 4. Computing devices 102 can be implemented on a server computer, virtual machine, container, cloud-computing platform, or other devices as would be appreciated by a person of ordinary skill in the art. Computing devices 102 can be implemented on a desktop computer, laptop, tablet, mobile device, smartphone, smartwatch, or other devices as would be appreciated by a person of ordinary skill in the art. Computing devices 102 can compute artificial intelligence algorithms used when providing or improving external stimuli (e.g., audio and/or physical stimuli) for a user.

Computing devices 102 can be communicatively coupled to one or more user input devices 104, biometric sensors 106, audio devices 108, and/or physical stimuli devices 110 through one or more communications channels, which can be wired, wireless, or a combination thereof. The communications channels can include any combination of Local Area Networks, Wide Area Networks, the Internet, Wi-Fi, Bluetooth, etc. Control logic or data can be transmitted to and from computing devices 102 via the communications channels. Computing devices 102 can be a component implemented at least partially within user input devices 104.

User input devices 104 can allow a user to provide information to a controlling application (e.g., mobile application system 502) for external stimuli capable of altering the user's mind-body state. User input devices 104 can also allow the controlling application to provide information to the user and can interact with various other devices, such as computing devices 102, biometric sensors 106, audio devices 108, and/or physical stimuli devices 110. User input devices 104 can be implemented on a desktop computer, laptop, tablet, mobile device, smartphone, smartwatch or other devices as would be appreciated by a person of ordinary skill in the art. User input devices 104 can have a display, such as a touch-sensitive display. For example, user input devices 104 can be a smartphone with a touch-sensitive display. User input devices 104 can include computing devices 102 or can communicate with computing devices 102.

User input devices 104 can be configured, in combination with computing devices 102, to provide an application to a user for altering the user's mind-body state through one or more external stimuli. In some embodiments, the application may be installed on the user input devices 104 and/or computing devices 102, and may be configured to receive user data and transmit information to biometric sensors 106, audio devices 108, and/or physical stimuli devices 110. The application can be configured to allow the user to onboard and/or register for the platform through one or more initial data entries. For example, the user can enter or select, via user input devices 104, one or more of personality traits, music preferences, a preferred time zone, or permission(s) for the application to access information from one or more third-party applications on user input devices 104. The personality trait information can include questions and answers corresponding to the five basic personality traits of extraversion, agreeableness, openness, conscientiousness, and emotional stability. The personality trait information can include questions and answers corresponding to other personality trait models. The personality trait information can be used by the application to curate an experience and provide external stimuli that is preferential to the user. For example, a user high in conscientiousness can dislike an intense and rebellious audio stimuli experience, and the application may provide an external stimuli comprising a reflective and complex audio stimuli experience to the user based on their preference. The music preference information can serve a similar purpose as the personality trait information. The music preference information can include preference on genre, instrumentation, arousal (i.e., preferred energy and intensity), valence (i.e., preferred emotional tone), depth (i.e., preferred intellectual sophistication of music), or whether the music is for guided or unguided practice (e.g., meditation or breathing). The time zone information can be useful in changing the provided experience based on the user's local time and day of the week. Access to information from one or more third-party applications on user input devices 104 can be useful in understanding the user's behaviors, activities (e.g., activity type, intensity, duration), and other information.

After onboarding the user, the application on user input devices 104 can be configured, in combination with computing devices 102, to receive a mind-body state goal from the user. The user's mind-body state goal can be a desired mind-body state or a desired performance goal, along with an available duration of time. Alternatively, the user's mind-body state goal can correspond to one or more mind-body goal categories (e.g., energizing, focusing, inspiring, relaxing, and sleeping). For example, the user's mind-body state goal can be a desire to feel more energized. Alternatively, the user's mind-body state goal can be a desire to have an increased heart rate. In either of these examples, the user can input the duration of time they have available to participate in the experience so that the application provides an appropriately timed experience.

Figure 2A:
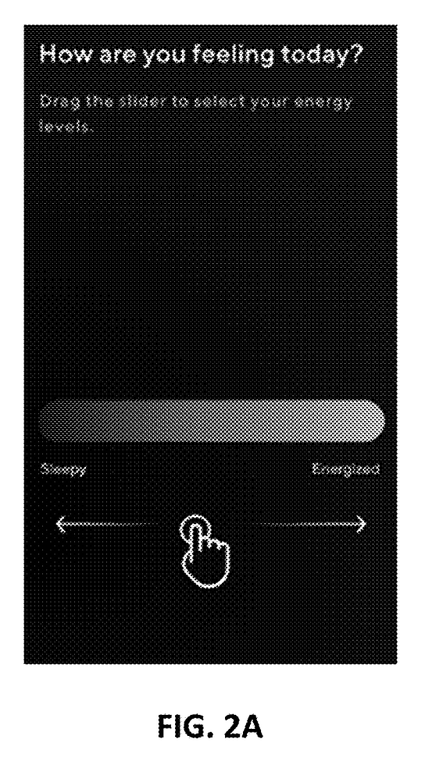
FIGS. 2A-2C are illustrations of visual analog scales on a user input device used when altering a user mind-body state through external stimuli, according to some aspects of the present disclosure.
Figure 2B:
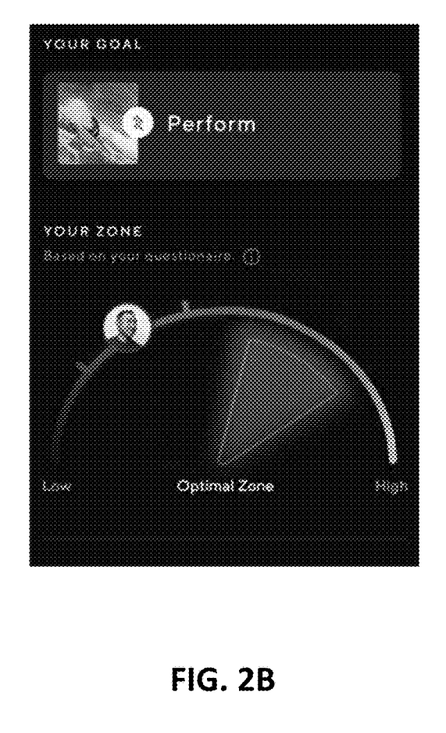
Figure 2C:
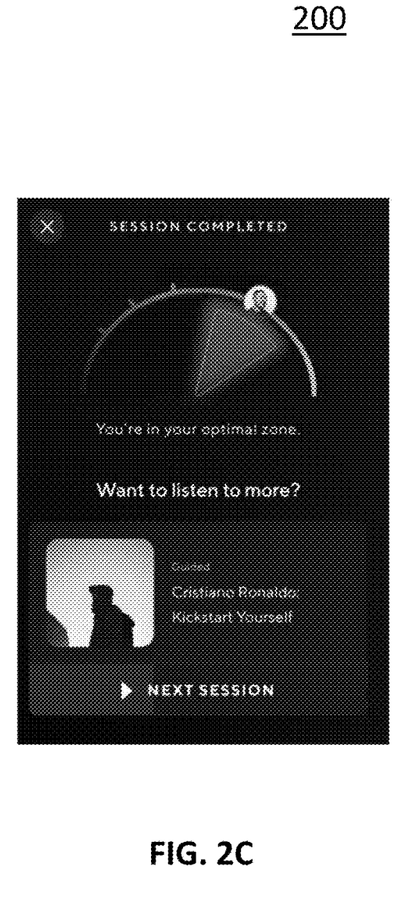

The application on user input devices 104 can then be configured, in combination with computing devices 102, to capture a current mind-body state of the user. The user's current mind-body state can correspond to one or more mind-body goal categories (e.g., energizing, focusing, inspiring, relaxing, and sleeping). The current mind-body state of the user can be determined by detecting at least one biometric parameter of the user using one or more biometric sensors 106, described below, and can also be determined by receiving another user input on user input devices 104 comprising answers to a questionnaire or feedback using a visual analog scale. The answers to a questionnaire can be indicative of certain levels of stress, anxiety, perceived exertion, pain intensity, cognitive performance (e.g., attention, focus, etc.), memory capacity, emotional regulation, mood, or sleep. In order to better understand the visual analog scale, reference is made to an example visual analog scale illustrated in FIG. 2A. FIGS. 2A-2C are illustrations of visual analog scales 200 on a user input device 104 used when altering a user mind-body state through external stimuli, according to some aspects of the present disclosure. In some embodiments, FIGS. 2A-2C represent example user interfaces presented by the application installed on the user input device 104. FIG. 2A is an example combination of a questionnaire and visual analog scale that allows the user to select, through a sliding bar, their energy levels using a touch-sensitive screen on user input devices 104. With this information, the application can provide a reference screen, as illustrated in FIG. 2B, showing the user their mind-body state goal and their current mind-body state.

Referring to FIG. 1, based on the data items received from the user, the user's mind-body state goal, and the user's current mind-body state, the application on user input devices 104 can be configured, in combination with computing devices 102, to provide external stimuli (e.g., audio and/or physical stimuli) to the user through audio devices 108 and/or physical stimuli devices 110. The external stimuli can be provided in mind-body goal categories that are a predetermined combination of audio protocols, physical protocols, and behavioral cues. For example, there can be five categories each aimed at providing a different outcome mind-body state to the user, including energizing, focusing, inspiring, relaxing, and sleeping mind-body states. When audio external stimuli is provided in categories, musical tracks are composed based on the predetermined combination of audio protocols, and the track is tagged based on the associated mind-body goal category. Provided by one or more audio devices 108 (described below), the audio protocols can include genre, tempo, key, tone, instrumentation, binaural beat, or duration. Provided by one or more physical stimuli devices 110 (described below), the physical protocols can include binaural rhythms, a device to be used, and specifications of the mechanical motion of the device (e.g., frequency, amplitude, torque, revolutions per minute, inflations per minute, percussions per minute, or vibrations per minute). The behavioral cues can be a prompt on user input devices 104, such as a prompt to breathe in accordance with a suggested rate. In some aspects, external stimuli options can be openly explored by the user on user input devices 104, separate from any configurations or processes.

In an example energizing category, the audio protocols can include a high tempo to match a heart rate of between 120-140 beats per minute. The key or tone can be generally described as a major mode, being happy and uplifting, and can have Marcato accentuation or Staccato articulation. The key or tone can be specifically described as D, F #, A, or B, or can occur at frequencies of 396 hertz, 417 hertz, or 639 hertz. The instrumentation can be rhythmic, with complex harmony and dissonance. And the binaural beat of the music can occur in the Beta frequency range. The physical protocols can match the binaural beat of the audio protocols, and can specify that a percussive massage device functions at 1800 percussions per minute.

In an example focusing category, the audio protocols can include a key or tone as B or Bm, or can occur at a pure 40 hertz or 741 hertz. The instrumentation can be pleasurable, at a non-specific genre, with relaxing background music. And the binaural beat of the music can occur in the Beta or Gamma frequency ranges. The physical protocols can match the binaural beat of the audio protocols, and can specify that a percussive massage device functions at 1800 percussions per minute (i.e. Beta), or 2100 or 2400 percussions per minute (i.e., Gamma).

In an example inspiring category, the audio protocols can include a high tempo. The key or tone can be generally described as a major mode, being happy and uplifting. The key or tone can be specifically described as C, C major, F, F #, A, or Bb, or can occur at frequencies of 417 hertz, 639 hertz, or 741 hertz. The instrumentation can be classical and percussive. And the binaural beat of the music can occur in the Alpha frequency range.

In an example relaxing category, the audio protocols can include a slow tempo with many pauses and rests, to match a heart rate of between 50-70 beats per minute. The key or tone can be generally described as a simple harmony, with consonance, light accentuation, and legato articulation. The key or tone can be specifically described as G, or can occur at frequencies of 432 hertz, 528 hertz, 396 hertz, 417 hertz, or 852 hertz. The instrumentation can include chants, such as Gregorian or Allegri, and instruments such as harps. And the binaural beat of the music can occur in the Theta or Alpha frequency ranges.

In an example sleeping category, the audio protocols can include a slow tempo to match a heart rate of between 40-50 beats per minute. The key or tone can be generally described as a simple harmony, with consonance, light accentuation, and legato articulation. The key or tone can be specifically described as Bm. The instrumentation can include ambient or nature sounds, and classical music. And the binaural beat of the music can occur in the Theta or Delta frequency ranges.

Alternatively to external stimuli being provided in categories, external stimuli can be provided based on a desired effect, such as a desire to lower heart rate by a certain rate of beats per minute. Regardless, the external stimuli can be provided to the user for a duration corresponding to the user's available duration of time or to a variance between the user's mind-body state goal and the user's current mind-body state. For example, if the user has 5 minutes of available time, the external stimuli can be less than 5 minutes. In another example, if the user's current mind-body state is stressed, but the user's mind-body state goal is relaxed, external stimuli can be provided for a longer duration. In an aspect, external stimuli is provided for at least 6 minutes to achieve an ideal altering of the user's mind-body state.

After the application on user input devices 104 has provided external stimuli to the user, the application can be configured, in combination with computing devices 102, to capture a new mind-body state of the user. Similar to capturing of the user's current mind-body state, the new mind-body state of the user can be determined by detecting at least one biometric parameter of the user using one or more biometric sensors 106, described below, and can also be determined by receiving another user input on user input devices 104 comprising answers to a questionnaire or feedback using a visual analog scale. The user's new mind-body state can correspond to one or more mind-body goal categories (e.g., energizing, focusing, inspiring, relaxing, and sleeping).

The application on user input devices 104 can then, in combination with computing devices 102, determine a similarity between the mind-body state goal and the new mind-body state, and recommend further external stimuli to the user based on the similarity. Determining a similarity between the mind-body state goal and the new mind-body state can be considered an examination of the effectiveness of the external stimuli in altering the mind-body state of the user. In other words, the application is determining what occurred during the session, whether what occurred was the anticipated occurrence, and what additional external stimuli should be recommended. If the mind-body state goal and the new mind-body state have moved closer together, then further external stimuli can be recommended that is similar to the original external stimuli. However, the further external stimuli can be the same or different as the original external stimuli provided. Referring to FIG. 2C, the application can provide a reference screen, as illustrated in FIG. 2C, showing the user their new mind-body state, the similarity between their mind-body state goal and their new mind-body state, and recommended further external stimuli.

The application on user input devices 104 can also contain an intelligent recommendation engine configured to provide personalized external stimuli (e.g., audio and/or physical stimuli) to the user. In combination with computing devices 102, the intelligent recommendation engine can consider at least one of a user's personality traits, music preference, time zone, duration of available time, or at least one biometric parameter when recommending further external stimuli to the user. If the user has used the application before, then the intelligent recommendation engine can also consider prior use of the external stimuli and its effectiveness in altering the user's mind-body state, use data, and a recommended device to be used with the user's mind-body state goal, when recommending external stimuli to the user. The use data can be measured during prior use by the user and can include various information, such as the minutes used, the songs played in use, the time of day the songs were played, etc.

Referring to FIG. 1, biometric sensors 106 can detect user mind-body states relevant when altering a user mind-body state through external stimuli. Biometric sensors 106 can be a sensor capable of detecting at least one biometric parameter, such as heart rate, heart rate variability, blood pressure, respiration, temperature, brain waves, acceleration, skin conductance, movement, sound, eye motion, muscle activity, pressure, touch, or emotion. For example, biometric sensors 106 can be a heart rate sensor (e.g., for detecting heart rate or heart rate variability), an electrocardiography sensor (e.g., for detecting heart activity), a blood pressure sensor (e.g., for detecting blood pressure), an electroencephalography sensor (e.g., for detecting brain waves), a tri-axes accelerometer (e.g., for detecting movement), a microphone (e.g., for detecting sound), an eye motion sensor (e.g., for detecting eye motion), a muscle activity sensor (e.g., for detecting muscle activity), a pressure sensor (e.g., for detecting pressure), a touch sensor (e.g., for measuring touch or contact), or a photoplethysmography sensor (e.g., for detecting emotion). Biometric sensors 106 can be coupled to the user by any fastening mechanism as would be appreciated by a person of ordinary skill in the art. Biometric sensors 106 can be any other sensor capable of detecting a biometric parameter as would be appreciated by a person of ordinary skill in the art. Biometric sensors 106 can be part of or separate from user input devices 104, audio devices 108, and/or physical stimuli devices 110. For example, biometric sensors 106 can be a heart rate sensor on a smartphone that is user input devices 104. In another example, biometric sensors 106 can be an external heart rate sensor that can communicate with computing devices 102.

Audio devices 108 can be used to provide audio external stimuli when altering a user mind-body state. Audio devices 108 can be a speaker or headphone device capable of outputting sound. As described above, audio devices 108 can be used to provide audio external stimuli that corresponds to certain audio protocols, including genre, tempo, key, tone, instrumentation, binaural beat, or duration. Tempo is how fast or slow a piece of music is played. Key or tone can be understood as a steady periodic sound, characterized by its pitch, duration, loudness, and timbre. Binaural beats can be considered auditory illusions that occur when a user listens to two different tones with slightly different frequencies at the same time. Binaural beats function when the two different tones have frequencies of less than 1000 hertz. A delta binaural beat is in the 0.5-4 hertz range, and is associated with deep sleep and relaxation. A theta binaural beat is in the 4-8 hertz range, and is associated with REM sleep, reduced anxiety, relaxation, meditative mind-body states, and creative mind-body states. An alpha binaural beat is in the range of 8-13 hertz, and is associated with relaxation, increased positivity, and decreased anxiety. A beta binaural beat is in the range of 14-30 hertz, and is associated with increased concentration, problem solving, and improved memory. A gamma binaural beat is in the range of 30-50 hertz, and is associated with maintenance of mental arousal while a person is awake. Audio devices 108 can be part of or separate from user input devices 104, biometric sensors 106, and/or physical stimuli devices 110. For example, audio devices 108 can be a speaker on a smartphone that is user input devices 104. In another example, audio devices 108 can be a tabletop speaker that can communicate with computing devices 102.

Physical stimuli devices 110 can be used to provide physical external stimuli when altering a user mind-body state. Physical stimuli devices 110 can be any device capable of providing an external stimulus to the surface of a user's body. Physical stimuli devices 110 can be a wearable garment, a compression device, an eye mask, a face mask, a percussive massage device, a vibration therapy device, a vibration therapy garment, a massage table, a massage pillow, a massage chair, a muscle stimulator, a blanket, a watch, a seating cover, or a standing mat. In some embodiments, the physical stimuli devices 110 may be a massage table with a transducer, such as any of the transducers disclosed in U.S. Pat. Nos. 7,418,108, 7,981,064, 8,077,884, 8,617,089, and 8,761,417. Each of the above mentioned patents, publications, and applications are incorporated herein by reference in their entireties, except for any definitions, subject matter disclaimers or disavowals, and except to the extent that the incorporated material is inconsistent with the express disclosure herein, in which case the language in this disclosure controls.

Suitable physical stimuli devices 110 can be, for example, percussive massage devices, such as those disclosed in U.S. Patent App. Pub. Nos. 2021/0244611, 2021/0022955, and 2020/0352821; vibration therapy devices, such as those disclosed in U.S. Patent App. Pub. No. 2021/0128399; electrical muscle stimulation devices, such as those disclosed in U.S. Pat. No. 10,881,849; percussive massage devices, such as those disclosed in U.S. Patent App. Pub. No. 2021/0401663A1; pneumatic compression devices, such as those disclosed in U.S. patent application Ser. No. 17/588,570; or eye massage devices, such as those disclosed in U.S. Provisional Patent App. No. 63/335,540, and U.S. patent application Ser. No. 17/933,419, filed on Sep. 19, 2022. Each of the above mentioned patents, publications, and applications are incorporated herein by reference in their entireties, except for any definitions, subject matter disclaimers or disavowals, and except to the extent that the incorporated material is inconsistent with the express disclosure herein, in which case the language in this disclosure controls.

Physical stimuli devices 110 can be a device providing an external stimulus that is at a certain frequency (e.g., vibrations per minute), amplitude, or torque. As described above, physical stimuli devices 110 can be used to provide physical external stimuli that corresponds to certain physical protocols, including binaural rhythms, a device to be used, and specifications of the mechanical motion of the device (e.g., frequency, amplitude, torque, revolutions per minute, inflations per minute, percussions per minute, or vibrations per minute). Physical stimuli devices 110 can function at a binaural rhythm corresponding to a binaural beat of audio devices 108. In other words, physical stimuli devices 110 can provide an external stimulus that is a vibration, percussion, massage, pressure, or any other external stimulus as would be appreciated by a person of ordinary skill in the art. Physical stimuli devices 110 can also be capable of providing varying levels of heat and light. For example, physical stimuli devices 110 can be a percussive massage device that is a massage gun that functions at varying rates of percussions per minute. In another example, physical stimuli devices 110 can be an eye mask with vibrations motors, air chambers, and heating pads. Physical stimuli devices 110 can be part of or separate from user input devices 104, biometric sensors 106, and/or audio devices 108. For example, physical stimuli devices 110 can be an eye mask that also has a heart rate sensor that is biometric sensors 106.

In another example, physical stimuli devices 110 can be a massage device that can communicate with computing devices 102.

Figure 3:
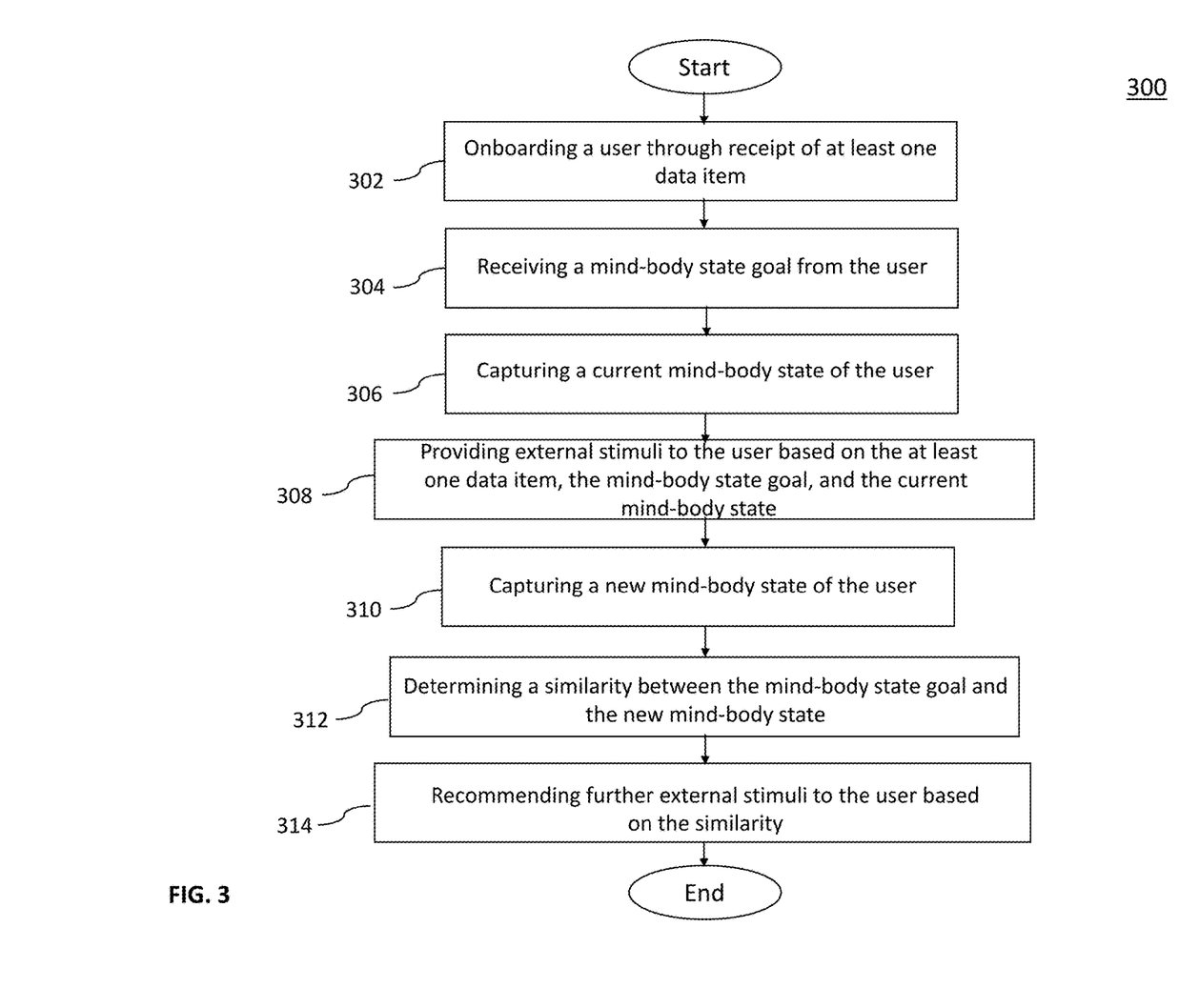
FIG. 3 is a flowchart of a method for altering a user mind-body state through external stimuli, according to some aspects of the present disclosure.

FIG. 3 is a flowchart for a method 300 for altering a user mind-body state through external stimuli, according to an aspect of the disclosure. It is to be appreciated that not all steps can be needed to perform the disclosure provided herein. Further, some of the steps can be performed simultaneously, or in a different order than shown in FIG. 3, as will be understood by a person of ordinary skill in the art.

Method 300 can be implemented by system 100 and operations caused by computing devices 102. However, method 300 is not limited to that example aspect.

In 302, a user is on-boarded through receipt of at least one data item. The user can provide the at least one data item through devices similar to user input devices 104. For example, the user can enter, via user input devices 104, personality traits, music preferences, time zone, or permission for the application to access information from one or more third-party applications on user input devices 104.

In 304, a mind-body state goal from the user is received. The user can provide the mind-body state goal through devices similar to user input devices 104. The user's mind-body state goal can be a desired mind-body state or a desired performance, along with an available duration of time. Alternatively, the user's mind-body state goal can correspond to one or more mind-body goal categories (e.g., energizing, focusing, inspiring, relaxing, and sleeping). For example, the user's mind-body state goal can be a desire to feel more energized. Alternatively, the user's mind-body state goal can be a desire to have an increased heart rate. In either of these examples, the user can input the duration of time they have available to participate in the experience so that the application provides an appropriately timed experience.

In 306, a current mind-body state of the user is captured. The current mind-body state of the user can be captured by devices similar to user input devices 104 and/or biometric sensors 106. The user's current mind-body state can correspond to one or more mind-body goal categories (e.g., energizing, focusing, inspiring, relaxing, and sleeping). The current mind-body state of the user can be determined by detecting at least one biometric parameter of the user using biometric sensors 106, and can also be determined by receiving another user input on user input devices 104 comprising answers to a questionnaire or feedback using a visual analog scale.

In 308, external stimuli (e.g., audio and/or physical stimuli) is provided to the user based on the at least one data item from 302, the mind-body state goal from 304, and the current mind-body state form 306. External stimuli can be provided to the user using audio devices 108, physical stimuli devices 110, and user input devices 104. The external stimuli can be provided in mind-body goal categories that are a predetermined combination of audio protocols, physical protocols, and behavioral cues. For example, there can be five categories each aimed at providing a different outcome mind-body state to the user, including energizing, focusing, inspiring, relaxing, and sleeping mind-body states. When audio external stimuli is provided in categories, musical tracks are composed based on the predetermined combination of audio protocols, and the track is tagged based on the associated mind-body goal category. Provided by audio devices 108, the audio protocols can include genre, tempo, key, tone, instrumentation, binaural beat, or duration. Provided by one or more physical stimuli devices 110, the physical protocols can include binaural rhythms, a device to be used, and specifications of the mechanical motion of the device (e.g., frequency, amplitude, torque, revolutions per minute, inflations per minute, percussions per minute, or vibrations per minute). The behavioral cues could be a prompt on user input devices 104, such as a prompt to breathe in accordance with a suggested rate.

Alternatively to external stimuli being provided in categories, external stimuli can be provided based on a desired effect, such as a desire to lower heart rate by a certain rate of beats per minute. Regardless, the external stimuli can be provided to the user for a duration corresponding to the user's available duration of time or to a variance between the user's mind-body state goal and the user's current mind-body state.

In 310, a new mind-body state of the user is captured. The new mind-body state of the user can be captured by devices similar to user input devices 104. Similar to capturing of the user's current mind-body state, the new mind-body state of the user can be determined by detecting at least one biometric parameter of the user using biometric sensors 106 and can also be determined by receiving another user input on user input devices 104 comprising answers to a questionnaire or feedback using a visual analog scale. The user's new mind-body state can correspond to one or more mind-body goal categories (e.g., energizing, focusing, inspiring, relaxing, and sleeping).

In 312, a similarity between the mind-body state goal from 304 and the new mind-body state from 310 is determined. The similarity between the mind-body state goal and the new mind-body state can be determined by devices similar to computing devices 102 and user input devices 104. Determining a similarity between the mind-body state goal and the new mind-body state can be considered an examination of the effectiveness of the external stimuli in altering the mind-body state of the user. In other words, the application is determining what occurred during the session, whether what occurred was the anticipated occurrence, and what additional external stimuli should be recommended.

In 314, further external stimuli is recommended to the user based on the similarity determination from 312. Further external stimuli can be recommended to the user by devices similar to computing devices 102 and user input devices 104. If the mind-body state goal and the new mind-body state have moved closer together, then further external stimuli can be recommended that is similar to the original external stimuli. However, the further external stimuli can be the same or different as the original external stimuli provided.

Figure 4:
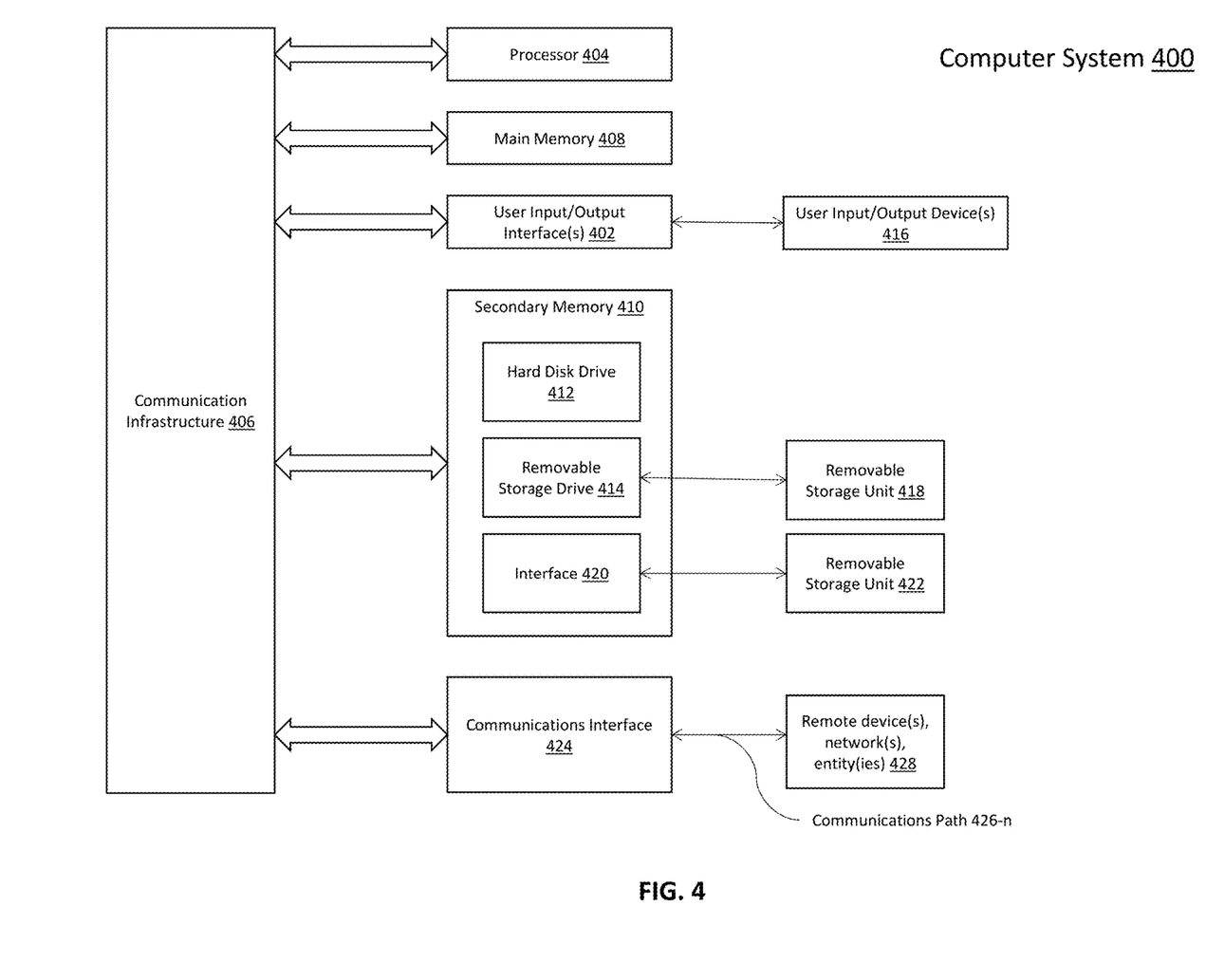
FIG. 4 is a block diagram of an example computer system useful for implementing various aspects.

Various aspects can be implemented, for example, using one or more computer systems, such as computer system 400 shown in FIG. 4. Computer system 400 can be used, for example, to implement a system for altering a user mind-body state through external stimuli. For example, computer system 400 can provide a multi-sensory experience with personalized external stimuli (e.g., audio and/or physical stimuli). Computer system 400 can be any computer capable of performing the functions described herein.

Computer system 400 can be any well-known computer capable of performing the functions described herein.

Computer system 400 includes one or more processors (also called central processing units, or CPUs), such as a processor 404. Processor 404 is connected to a communication infrastructure or bus 406.

One or more processors 404 can each be a graphics processing unit (GPU). In an aspect, a GPU is a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computer system 400 also includes user input/output device(s) 416, such as monitors, keyboards, pointing devices, etc., that communicate with communication infrastructure 406 through user input/output interface(s) 402.

Computer system 400 also includes a main or primary memory 408, such as random access memory (RAM). Main memory 408 can include one or more levels of cache. Main memory 408 has stored therein control logic (i.e., computer software) and/or data.

Computer system 400 can also include one or more secondary storage devices or memory 410. Secondary memory 410 can include, for example, a hard disk drive 412 and/or a removable storage device or drive 414. Removable storage drive 414 can be a floppy disk drive, a magnetic tape drive, a compact disk drive, an optical storage device, tape backup device, and/or any other storage device/drive.

Removable storage drive 414 can interact with a removable storage unit 418. Removable storage unit 418 includes a computer usable or readable storage device having stored thereon computer software (control logic) and/or data. Removable storage unit 418 can be a floppy disk, magnetic tape, compact disk, DVD, optical storage disk, and/any other computer data storage device. Removable storage drive 414 reads from and/or writes to removable storage unit 418 in a well-known manner.

According to an exemplary aspect, secondary memory 410 can include other means, instrumentalities or other approaches for allowing computer programs and/or other instructions and/or data to be accessed by computer system 400. Such means, instrumentalities or other approaches can include, for example, a removable storage unit 422 and an interface 420. Examples of the removable storage unit 422 and the interface 420 can include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 400 can further include a communication or network interface 424. Communication interface 424 enables computer system 400 to communicate and interact with any combination of remote devices, remote networks, remote entities, etc. (individually and collectively referenced by reference number 428). For example, communication interface 424 can allow computer system 400 to communicate with remote devices 428 over communications path 426, which can be wired and/or wireless, and which can include any combination of LANs, WANs, the Internet, etc. Control logic and/or data can be transmitted to and from computer system 400 via communication path 426.

In an aspect, a tangible, non-transitory apparatus or article of manufacture comprising a tangible, non-transitory computer useable or readable medium having control logic (software) stored thereon is also referred to herein as a computer program product or program storage device. This includes, but is not limited to, computer system 400, main memory 408, secondary memory 410, and removable storage units 418 and 422, as well as tangible articles of manufacture embodying any combination of the foregoing. Such control logic, when executed by one or more data processing devices (such as computer system 400), causes such data processing devices to operate as described herein.

Based on the teachings contained in this disclosure, it will be apparent to persons skilled in the relevant art(s) how to make and use aspects of this disclosure using data processing devices, computer systems and/or computer architectures other than that shown in FIG. 4. In particular, aspects can operate with software, hardware, and/or operating system implementations other than those described herein.

Figure 5:
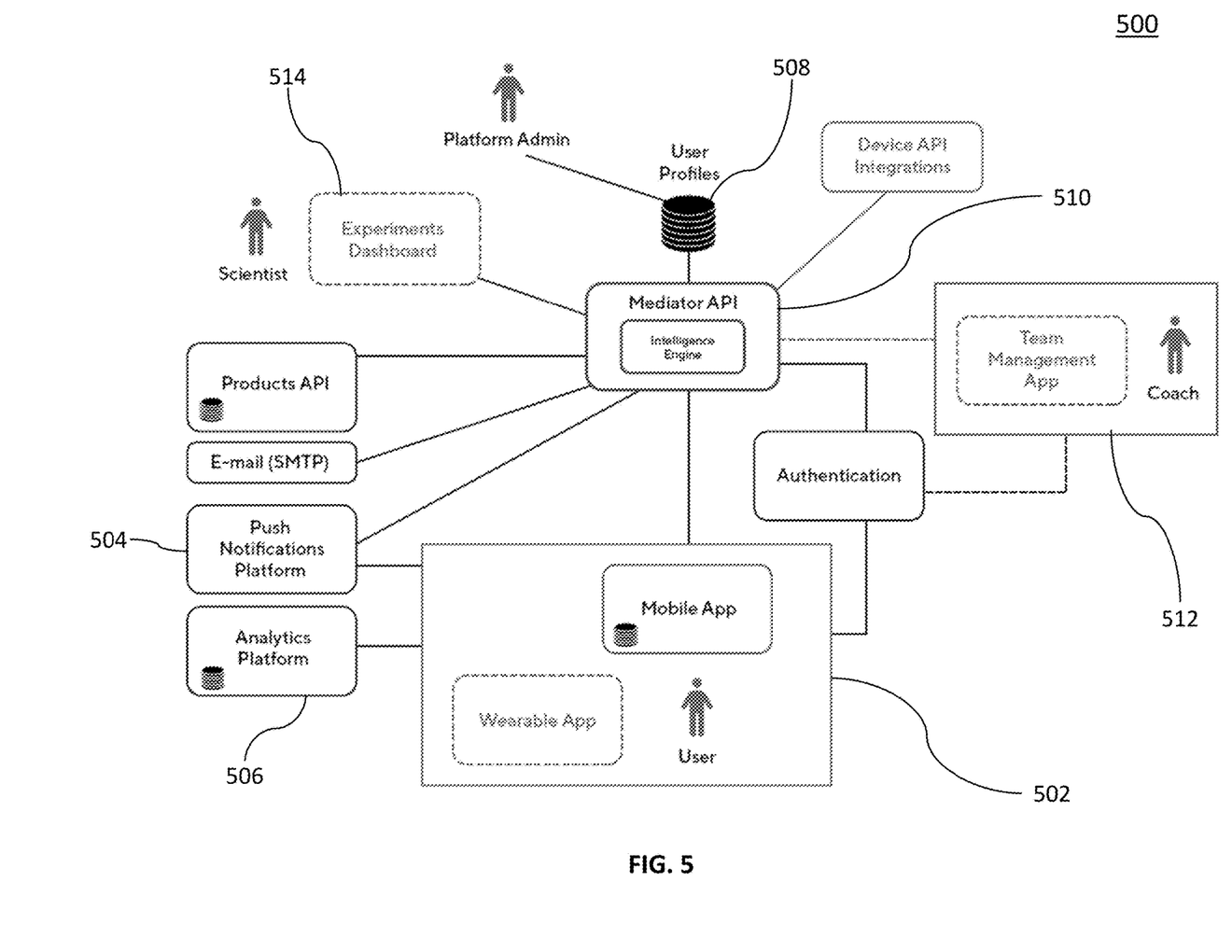
FIG. 5 is a block diagram of an application system for altering a user mind-body state through external stimuli, according to some aspects of the present disclosure.

FIG. 5 is a block diagram of an application system 500 for altering a user mind-body state through external stimuli, according to some aspects of the present disclosure. System 500 can include a mobile application system 502, a push notifications platform 504, an analytics platform 506, a user profiles database 508, a mediator application programming interface (API), a team management application system 512, an experiments dashboard 514, and various other components, such as a products API, an E-mail system, an authentication system, a device API integration system, or other components as would be appreciated by a person of ordinary skill in the art.

Mobile application system 502 can be an application on a user's personal device when accessing a service for altering a user mind-body state through external stimuli. Mobile application system 502 can be the application described above with reference to FIGS. 1-3. Mobile application system 502 can include a database and other applications configured to control external stimuli devices. Mobile application system 502 can interact with various other systems, such as push notifications platform 504 or analytics platform 506.

Push notifications platform 504 can provide notifications to the user's personal device through mobile application system 502. Analytics platform 506 can include a database and can interact with mobile application system 502 to provide local processing for altering a user mind-body state through external stimuli.

Mobile application system 502 can also interact with mediator API 510 and an authentication system for verifying and authenticating a user's identity. Mediator API 510 can include an intelligence engine, such as the intelligent recommendation engine described above with reference to FIGS. 1-3. Mediator API 510 can manage interactions between mobile application system 502 and other systems when altering a user mind-body state through external stimuli. Mediator API 510 can interface with push notifications platform 504, analytics platform 506, a products API, an E-mail system, or a device API integration system. Mediator API 510 can interface with user profiles database 508 that stores information corresponding to a plurality of users accessing respective mobile application systems 502 or team management application systems 512. Mediator API 510 can also interface with a team management application system 512 and an experiments dashboard 514.

Team management application system 512 can be similar to mobile application system 502, but can be configured for use by an instructor or coach who aims to alter user mind-body states of a group of people or players through external stimuli. Experiments dashboard 514 can be accessed by scientists or other professionals to provide updated content to system 500. For example, experiments dashboard 514 can be used to provide an updated audio and/or physical stimuli to users based on new research linking an audio and/or physical criteria with alteration in user mind-body states.

Figure 6:
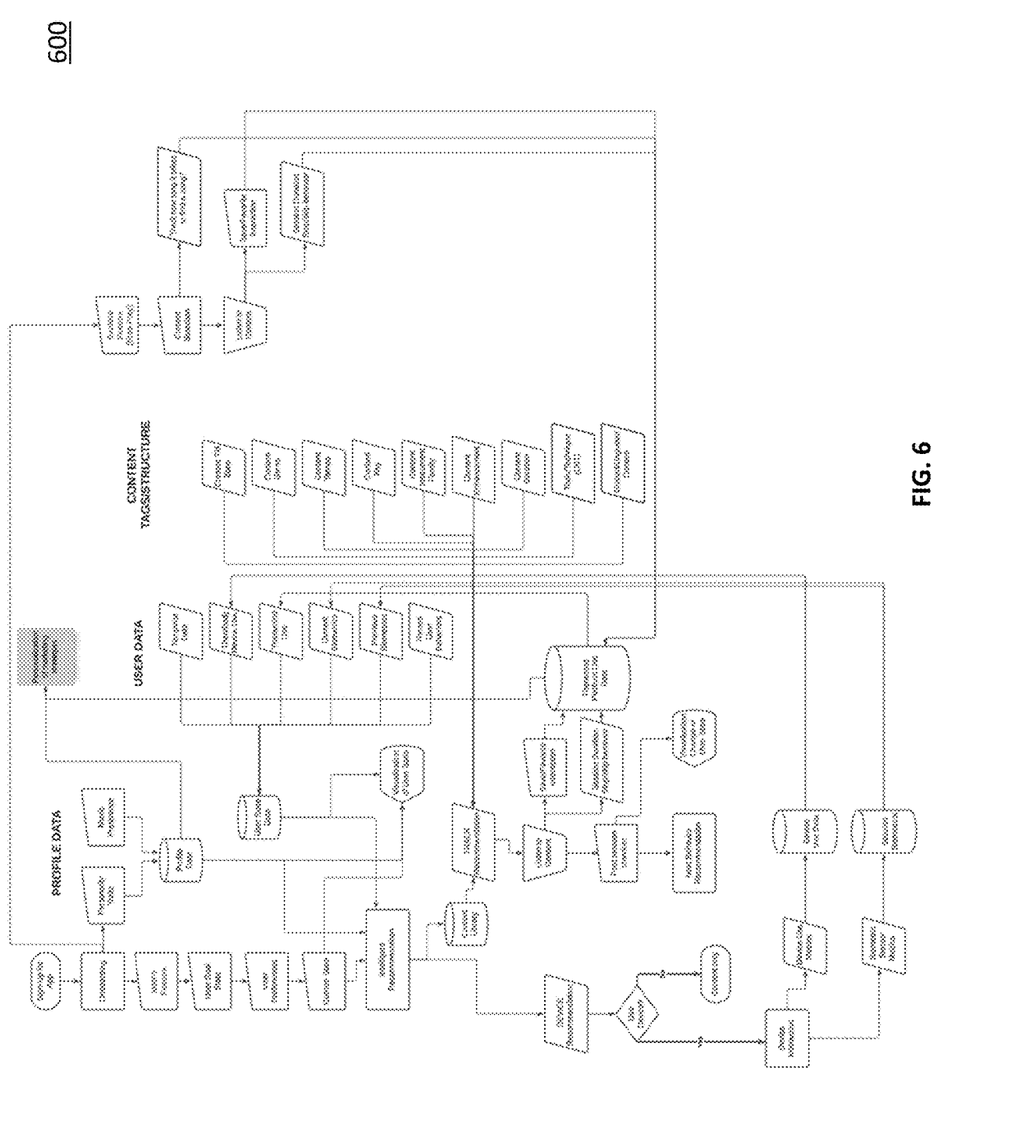
FIG. 6 is a flowchart of a system for altering a user mind-body state through external stimuli, according to some aspects of the present disclosure.

FIG. 6 is a flowchart of a system 600 for altering a user mind-body state through external stimuli, according to some aspects of the present disclosure. The system is initiated when a user signs up for the application (e.g., mobile application system 502) for altering their mind-body state through external stimuli. The user is prompted to onboard, where they can input information such as personality traits or music preference. This information is stored in a profile database and can be used to personalize marketing to the user or throughout system 600. After onboarding, the user provides additional information, such as their mind-body state goal and their content preferences. This is then compared, by system 600, to their current state. In some aspects, system 600 can include an intelligent recommendation engine (e.g., in mediator API 510) to recommend certain audio and/or physical stimuli to the user based on their mind-body state goal and current mind-body state. When using the intelligent recommendation engine or otherwise, the user can then be recommended a device to use to receive physical stimuli and/or a musical track to receive audio stimuli from a content library. When using the intelligent recommendation engine or otherwise, user state data can be used to curate audio and/or physical stimuli to the user. For example, temporal data, device use data, current user biometrics, previous user biometrics, or user behavior data can also be used when providing stimuli to the user.

With respect to the device recommendation for receiving physical stimuli, the user can select whether to use the device or to only receive audio stimuli from the content library. If the user selects to use the device, the device can provide various physical stimuli. Use of the device will produce device use metrics and biometric sensor metrics that can be recorded in respective databases related to previous user biometrics.

With respect to the musical track for receiving audio stimuli, the user can listen to the content. The type of musical track recommended can be retrieved based on tags within the data of the content or the structure of the content. For example, content can be recommended based on zone, genre, tempo, key, instrument family, desired enhancement, duration, topic, technique, or whether it is guided or unguided. After listening, the user can be provided with a post-session check-in, useful when recommending subsequent content or when presenting a graphic to the user (e.g., FIGS. 2A-2C) so that they can visualize the change of user mind-body state. Additionally, the user can have the ability to save or favorite the content, can alter the duration of the content, or can stop or skip the content. Any such behavior by the user can be recorded as use data relevant for personalization of marketing or throughout system 600.

The user also has the option to freely explore the features of system 600. For example, the user can select content themselves and can listen to this content. Meanwhile, system 600 can track the user's process in selecting the content, or any duration, stop, or skip behavior of the user. This information can be used to better curate system 600 to the user.

It is to be appreciated that the Detailed Description section, and not any other section, is intended to be used to interpret the claims. Other sections can set forth one or more but not all exemplary aspects as contemplated by the inventor(s), and thus, are not intended to limit this disclosure or the appended claims in any way.

While this disclosure describes exemplary aspects for exemplary fields and applications, it should be understood that the disclosure is not limited thereto. Other aspects and modifications thereto are possible, and are within the scope and spirit of this disclosure. For example, and without limiting the generality of this paragraph, aspects are not limited to the software, hardware, firmware, and/or entities illustrated in the figures and/or described herein. Further, aspects (whether or not explicitly described herein) have significant utility to fields and applications beyond the examples described herein.

Aspects have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative aspects can perform functional blocks, steps, operations, methods, etc. using orderings different than those described herein.

References herein to "one aspect," "an aspect," "an example aspect," or similar phrases, indicate that the aspect described can include a particular feature, structure, or characteristic, but every aspect can not necessarily include the particular feature, structure, or characteristic. Moreover, such phrases are not necessarily referring to the same aspect. Further, when a particular feature, structure, or characteristic is described in connection with an aspect, it would be within the knowledge of persons skilled in the relevant art(s) to incorporate such feature, structure, or characteristic into other aspects whether or not explicitly mentioned or described herein. Additionally, some aspects can be described using the expression "coupled" and "connected" along with their derivatives. These terms are not necessarily intended as synonyms for each other. For example, some aspects can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary aspects, but should be defined only in accordance with the following claims and their equivalents.

What is claimed is:

1. A method for altering a user mind-body state through external stimuli, comprising:
   onboarding a user through receipt of at least one data item;
   receiving a mind-body state goal from the user, wherein the mind-body state goal corresponds to a selected category comprising a predetermined combination of audio protocols, physical protocols, and behavioral cues;
   capturing a current mind-body state of the user;
   providing external stimuli to the user based on the at least one data item, the mind-body state goal, and the current mind-body state;
   capturing a new mind-body state of the user;
   determining a similarity between the mind-body state goal and the new mind-body state; and
   recommending further external stimuli to the user based on the similarity,
   wherein the recommended external stimuli is a physical protocol using a recommended physical stimuli device among a predetermined plurality of physical stimuli devices, and
   wherein the physical protocol includes inflations per minute.

2. The method of claim 1, wherein the at least one data item comprises the user's personality traits, music preference, time zone, and/or information from one or more third-party applications.

3. The method of claim 1, wherein the physical protocol further includes frequency, amplitude, torque, revolutions per minute, percussions per minute, and/or vibrations per minute.

4. The method of claim 1, wherein the mind-body state goal is provided through user input of a desired mind-body state, a desired performance, and/or a duration of time.

5. The method of claim 1, wherein capturing the current mind-body state or capturing the new mind-body state comprises at least one of:
   detecting at least one biometric parameter of the user using a biometric sensor coupled to the user; or
   receiving a user input comprising answers to a questionnaire or feedback using a visual analog scale.

6. The method of claim 5, wherein the biometric sensor detects at least one biometric parameter, including heart rate, heart rate variability, blood pressure, respiration, temperature, brain waves, movement, skin conductance, sound, or emotion.

7. The method of claim 1, wherein the predetermined plurality of physical stimuli devices includes one or more of:
   a wearable garment; a compression device; an eye mask; a face mask; a percussive massage device; a vibration therapy device; a vibration therapy garment; a massage table; a massage pillow; a massage chair; a blanket; a watch; a seating cover; or a standing mat.

8. The method of claim 1, wherein the external stimuli is provided for greater than five but less than ten minutes.

9. The method of claim 1, wherein the external stimuli is provided based on a variance between the mind-body state goal and the current mind-body state.

10. The method of claim 1, wherein recommending further external stimuli to the user is also based on an intelligent recommendation engine, wherein the intelligent recommendation engine is configured to provide personalized external stimuli to the user based on at least one of:
    personality traits;
    music preference;
    time zone;
    duration of time;
    at least one biometric parameter;
    prior use of the external stimuli;
    use data; or
    a recommended device to be used with the user's mind-body state goal.

11. The method of claim 1, wherein the selected category comprises selecting a category from a group of mind-body goal categories including energizing, focusing, inspiring, relaxing, and sleeping.

12. A system for altering a user mind-body state through external stimuli, comprising:
    a user input device;
    a biometric sensor;
    an audio device;
    a physical stimuli device, the physical stimuli device being an eye mask; and
    a computing device coupled to the user input device, the biometric sensor, the audio device, and the physical stimuli device, comprising:
    a processor; and
    a memory, wherein the memory contains instructions stored thereon that when executed by the processor cause the computing device to:
    onboard a user through receipt of at least one data item from the user input device;
    receive a mind-body state goal from the user through the user input device;

capture a current mind-body state of the user through the user input device and/or the biometric sensor;
provide external stimuli to the user based on the at least one data item, the mind-body state goal, and the current mind-body state through the audio device, the physical stimuli device, and/or the user input device;
capture a new mind-body state of the user through the user input device and/or the biometric sensor;
determine a similarity between the mind-body state goal and the new mind-body state; and
recommend further external stimuli to the user through the user input device based on the similarity,
wherein the external stimuli provided to the user is a physical protocol including inflations per minute based on biometric data from the biometric sensor.

13. The system of claim 12, wherein the external stimuli, the mind-body state goal, the current mind-body state, or the new mind-body state corresponds to a category that is a predetermined combination of audio protocols, physical protocols, and behavioral cues, wherein the audio protocols include genre, tempo, key, tone, instrumentation, binaural beat, and/or duration, and wherein the physical protocols further include frequency, amplitude, and/or vibrations per minute.

14. The system of claim 12, wherein the external stimuli is audio and/or physical stimuli provided to the user through the audio device and/or the physical stimuli device, and wherein the audio device is a speaker or headphones.

15. The system of claim 12, wherein recommending further external stimuli to the user is also based on an intelligent recommendation engine, wherein the intelligent recommendation engine is configured to provide personalized external stimuli to the user based on at least one of:
personality traits;
music preference;
time zone;
duration of time;
at least one biometric parameter;
prior use of the external stimuli;
use data; or
a recommended device to be used with the user's mind-body state goal.

16. A non-transitory computer-readable medium having instructions stored thereon that, when executed by at least one computing device, cause the at least one computing device to perform operations comprising:
onboarding a user through receipt of at least one data item;
receiving a mind-body state goal from the user, wherein the mind-body state goal corresponds to a selected category that is a predetermined combination of audio protocols, physical protocols, and behavioral cues;
capturing a current mind-body state of the user;
providing external stimuli to the user based on the at least one data item, the mind-body state goal, and the current mind-body state;
capturing a new mind-body state of the user;
determining a similarity between the mind-body state goal and the new mind-body state; and
recommending further external stimuli to the user based on the similarity,
wherein the external stimuli, the current mind-body state, or the new mind-body state corresponds to the selected category that is the predetermined combination of audio protocols, physical protocols, and behavioral cues, and
wherein the audio protocols include binaural beats.

17. The non-transitory computer-readable medium of claim 16, wherein a physical protocol is configured to match the binaural beats of the audio protocol.

* * * * *

UNITED STATES PATENT AND TRADEMARK OFFICE
CERTIFICATE OF CORRECTION

| | | |
|---|---|---|
| PATENT NO. | : 12,017,009 B2 | Page 1 of 1 |
| APPLICATION NO. | : 17/933423 | |
| DATED | : June 25, 2024 | |
| INVENTOR(S) | : McVey et al. | |

It is certified that error appears in the above-identified patent and that said Letters Patent is hereby corrected as shown below:

On the Title Page

Item (72), in "Inventors", Line 9, after "CA (US)" insert -- Benjamin Andrew Soldate, Burbank, CA (US) --.

Signed and Sealed this
Tenth Day of September, 2024

Katherine Kelly Vidal
*Director of the United States Patent and Trademark Office*